US007947805B2

(12) United States Patent
Belloir et al.

(10) Patent No.: US 7,947,805 B2

(45) Date of Patent: May 24, 2011

(54) BCMA POLYPEPTIDES AND USES THEREOF

(75) Inventors: Benedicte Belloir, Corbeil-Essonnes (FR); Anne-Francoise Cledat, Echarcon (FR); Gwenael Primas, Anvers St. Georges (FR)

(73) Assignee: Merck Serono S.A., Coinsins, Vaud (CH)

( * ) Notice: Subject to any disclaimer, the term of this patent is extended or adjusted under 35 U.S.C. 154(b) by 668 days.

(21) Appl. No.: 11/722,533

(22) PCT Filed: Dec. 22, 2005

(86) PCT No.: PCT/EP2005/057091

§ 371 (c)(1), (2), (4) Date: Jun. 22, 2007

(87) PCT Pub. No.: WO2006/067210

PCT Pub. Date: Jun. 29, 2006

(65) Prior Publication Data

US 2009/0191203 A1 Jul. 30, 2009

(30) Foreign Application Priority Data

Dec. 23, 2004 (EP) .................................... 04293108

(51) Int. Cl.

| | |
|---|---|
| ***C07K 14/00*** | (2006.01) |
| ***C07H 21/04*** | (2006.01) |
| ***C12N 15/09*** | (2006.01) |
| ***C12N 15/12*** | (2006.01) |
| ***A61K 38/16*** | (2006.01) |
| ***A61P 35/00*** | (2006.01) |

(52) U.S. Cl. ..... 530/350; 536/23.5; 536/23.4; 435/69.1; 435/69.7; 424/130.1; 424/139.1; 424/143.1; 424/185.1; 514/1.1; 514/19.3; 514/21.2

(58) Field of Classification Search ........................ None
See application file for complete search history.

(56) References Cited

U.S. PATENT DOCUMENTS

| | | | | |
|---|---|---|---|---|
| 7,083,785 | B2 * | 8/2006 | Browning et al. | 424/130.1 |
| 7,276,241 | B2 * | 10/2007 | Schneider et al. | 424/185.1 |
| 2006/0286093 | A1 * | 12/2006 | Gross et al. | 424/133.1 |

FOREIGN PATENT DOCUMENTS

| | | | |
|---|---|---|---|
| WO | WO 00/68378 | A1 | 11/2000 |
| WO | WO 01/12812 | A2 | 2/2001 |
| WO | WO 01/24811 | A1 | 4/2001 |
| WO | WO 01/87977 | A2 | 11/2001 |
| WO | WO 03/072713 | A2 | 9/2003 |

OTHER PUBLICATIONS

Smirmova et al., Mol Immunol. Feb. 2008;45(4):1179-1183.*

Database EMBL 'Online', Database Accession No. BG183381, "RST2275 Athersys RAGE Library Homo sapiens cDNA, mRNA sequence", Apr. 26, 2001, vol. 19, No. 5, XP002323758, pp. 1-2.

Gross, J. et al. "TACI and BCMA are receptors for a TNF homologue implicated in B-cell autoimmune disease", *Nature*, Apr. 27, 2000, pp. 995-999, vol. 404.

Hatzoglou, A. et al. "TNF Receptor Family Member BCMA (B Cell Maturation) Associates with TNF Receptor-Associated Factor (TRAF) 1, TRAF2, and TRAF3 and Activates NF-KB, Elk-1, c-Jun N-Terminal Kinase, and p38 Mitogen-Activated Protein Kinase", *Journal of Immunology*, Aug. 1, 2000, pp. 1322-1330, vol. 165, No. 3.

Khare, S. et al. "Severe B cell Hyperplasia and autoimmune disease in TALL-1 transgenic mice", *Proc. Natl. Acad. Sci. USA*, Mar. 28, 2000, pp. 3370-3375, vol. 97, No. 7.

Kim, H. et al. "Crystal structure of the BAFF-BAFF-R complex and its implications for receptor activation", *Nature Structural Biology*, May 2003, pp. 342-348, vol. 10, No. 5.

Laabi, Y. et al. "A new gene, BCM, on chromosome 16 is fused to the interleukin 2 gene by a t(4;16)(q26;p13) translocation in a malignant T cell lymphoma", *The EMBO Journal*, Nov. 1992, pp. 3897-3904, vol. 11, No. 11.

Laabi, Y. et al. "The BCMA gene, preferentially expressed during B lymphoid maturation, is bidirectionally transcribed", *Nucleic Acids Research*, 1994, pp. 1147-1154, vol. 22, No. 7.

Liu, Y. et *a/*. "Ligand-receptor binding revealed by the TNF family member TALL-1", *Nature*, May 1, 2003, pp. 49-56, vol. 423.

Mackay, F. etal. "The TNF family members BAFF and APRIL: the growing complexity", *Cytokine & Growth Factor Reviews*, 2003, pp. 311-324, vol. 14, Nos. 3-4.

Mackay, F. et al. "Mice Transgenic for BAFF Develop Lymphocytic Disorders Along with Autoimmune Manifestations", *J. Exp. Med.*, Dec. 6, 1999, pp. 1697-1710, vol. 190, No. 11.

Mackay, F. et al. "BAFF and APRIL: A Tutorial on B Cell Survival", *Annu. Rev. Immunol.*, 2003, pp. 231-264, vol. 21.

Madry, C. et al. "The characterization of murine BCMA gene defines it as a new member of the tumor necrosis factor receptor superfamily", *International Immunology*, Nov. 1998, pp. 1693-1702, vol. 10, No. 11.

Marsters, S. et al. "Interaction of the TNF homologues BLyS and APRIL with the TNF receptor homologues BCMA and TACI", *Current Biology*, Jun. 29, 2000, pp. 785-788, vol. 10, No. 13.

O'Connor, B. et al. "BCMA Is Essential for the Survival of Long-lived Bone Marrow Plasma Cells", *J. Exp. Med.*, Jan. 5, 2004, pp. 91-97 vol. 199, No. 1.

Patel, D. etal. "Engineering an APRIL-specific B Cell Maturation Antigen", *The Journal of Biological Chemistry*, Apr. 16, 2004, pp. 16727-16735, vol. 279, No. 16.

Pelletier, M. et al. "Comparison of Soluble Decoy IgG Fusion Proteins of BAFF-R and BCMA as Antagonists for BAFF", *The Journal of Biological Chemistry*, Aug. 29, 2003, pp. 33127-33133, vol. 278, No. 35.

(Continued)

*Primary Examiner* — David S Romeo

*Assistant Examiner* — Daniel C Gamett

(74) *Attorney, Agent, or Firm* — Saliwanchik, Lloyd & Eisenschenk

(57) ABSTRACT

The present invention relates to BCMA polypeptide variants and their uses, particularly for therapeutic or prophylactic treatment in human subjects. The invention also relates to nucleic acids encoding said polypeptides, vectors comprising such nucleic acids and recombinant cells containing the same. The invention further discloses methods of producing such polypeptides, as well as methods and tools for detecting or dosing these polypeptides in any sample.

46 Claims, 3 Drawing Sheets

OTHER PUBLICATIONS

Figure 1:
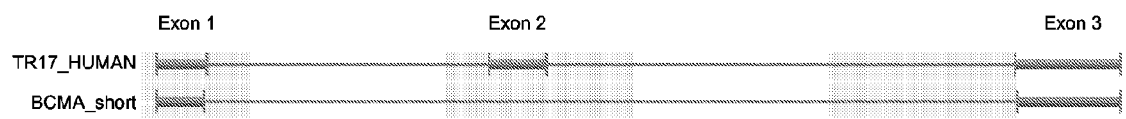

Rennert. P. et al. "A Soluble Form of B Cell Maturation Antigen, a Receptor for the Tumor Necrosis Factor Family Member APRIL, Inhibits Tumor Cell Growth", *J. Exp. Med.*, Dec. 4, 2000, pp. 1677-1683, vol. 192, No. 11.

Shu, H.-B. et al. "B cell maturation protein is a receptor for the tumor necrosis factor family member TALL-1", *Proc. Natl. Acad. Sci. USA*, Aug. 1, 2000, pp. 9156-9161, vol. 97, No. 16.

Wallweber, H. et al. "The Crystal Structure of a Proliferation-inducing Ligand, APRIL", *J. Mol. Biol.*, Oct. 15, 2004, pp. 283-290, vol. 343.

Xu, S. et a/. "B-Cell Maturation Protein, Which Binds the Tumor Necrosis Factor Family Members BAFF and APRIL, Is Dispensable for Humoral Immune Responses", *Molecular and Cellular Biology*, Jun. 2001, pp. 4067-4074, vol. 21, No. 12.

Yu, G. et al. "APRIL and TALL-1 and receptors BCMA and TACI: system for regulating humoral immunity", *Nature Immunology*, Sep. 2000, pp. 252-256, vol. 1, No. 3.

* cited by examiner

```
TR17_MOUSE              ---MAQQCFHSEYFDSLLHACKPCHLRCSN--PPATCQPYCDPSVTSSVKGTYTVLWIFL 55
TR17_MOUSE_isoform2     ---MAQQCFHSEYFDSLLHACKPCHLRCSN--PPATCQPYCDPSVTSSVKGTYTVLWIFL 55
TR17_HUMAN              MLQMAGQCSQNEYFDSLLHACIPCQLRCSSNTPPLTCQRYCNASVTNSVKGTNAILWTCL 60
BCMA_short              MLQMAGQCSQNEYFDSLLHACIPCQLRCSSNTPPLTCQRYCNA----------------- 43
                           ** ** :.********** **:****.  ** *** **:.

TR17_MOUSE              GLTLVLSLALFTISFLLRKMNPEALKDEPQSPGQLDGSAQLDKADTELTRIRAGDDRIFP
115
TR17_MOUSE_isoform2     GLTLVLSLALFTISFLLRKMNPEALKDEPQS-----GSAQLDKADTELTRIRAGDDRIFP
110
TR17_HUMAN              GLSLIISLAVFVLMFLLRKISSEPLKDEFKNT----GSGLLGMANIDLEKSRTGDEIILP
116
BCMA_short              ------------------------------------RSGLLGMANIDLEKSRTGDEIILP 67
                                                             *. *. *: :* : *:**: *:*

TR17_MOUSE              RSLEYTVEECTCEDCVKSKPKGDSDHFFPLPAMEEGATILVTTKTGDYGKSSVPTALQSV
175
TR17_MOUSE_isoform2     RSLEYTVEECTCEDCVKSKPKGDSDHFFPLPAMEEGATILVTTKTGDYGKSSVPTALQSV
170
TR17_HUMAN              RGLEYTVEECTCEDCIKSKPKVDSDHCFPLPAMEEGATILVTTKTNDYCKS-LPAALS-A
174
BCMA_short              RGLEYTVEECTCEDCIKSKPKVDSDHCFPLPAMEEGATILVTTKTNDYCKS-LPAALS-A
125
                        *.*************:***** **** ******************.** ** :*:**. .

TR17_MOUSE              MGMEKPTHTR 185
TR17_MOUSE_isoform2     MGMEKPTHTR 180
TR17_HUMAN              TEIEKSISAR 184
BCMA_short              TEIEKSISAR 135
                          :**.  :*
```

Figure 2

BCMA POLYPEPTIDES AND USES THEREOF

CROSS-REFERENCE TO RELATED APPLICATION

This application is the U.S. national stage application of International Patent Application No. PCT/EP2005/057091, filed Dec. 22, 2005, the disclosure of which is hereby incorporated by reference in its entirety, including all figures, tables and amino acid or nucleic acid sequences.

The present invention relates to B Cell Maturation Antigen polypeptides and their uses, particularly for therapeutic or prophylactic treatment in human subjects. The invention also relates to nucleic acids encoding said polypeptides, vectors comprising such nucleic acids and recombinant cells containing the same, as well as corresponding pharmaceutical compositions. The invention further discloses methods of producing such polypeptides, as well as methods and tools for detecting or dosing these polypeptides in any sample.

BACKGROUND

B cell maturation antigen, also known as BCMA; TR17_HUMAN, TNFRSF17 (Swissprot Acc. number Q02223), is a member of the tumor necrosis receptor superfamily that is preferentially expressed in mature B cells [Laabi et al. 1992; Madry et al. 1998]. BCMA is a non glycosylated type III transmembrane protein, which is involved in B cell maturation, growth and survival.

The human BCMA protein is a 184 amino acid polypeptide comprising an extracellular domain, located within the N-terminal region of the protein (amino acid residues 1-50), an intracellular domain (amino acid residues 94-184) and a transmembrane region (amino acid residues 51-93). The extracellular domain of BCMA comprises a six-cysteine-rich motif (characteristic of TNF-R molecules). This domain, although weakly similar to the consensus matrix of the cysteine-rich domain (CRD) mainly found on receptors for growth factors, still binds the TNF like protein. However, unlike some of the members of tumor necrosis necrosis receptor superfamily, BCMA intracellular region lacks a "death domain", which is involved in TNF-mediated cell death signalling. The intracellular region, however, contains a 25 amino acid fragment (residues 119-143) that is essential for association with the TRAFs and activation of NF-κB. Since BCMA is a Type III transmembrane protein (i.e. the same sequence acts as both transmembrane and signal sequence), the BCMA gene does not contain a specific signal peptide sequence so that, under physiological conditions, the protein is mostly expressed within the Golgi membranes and not at the cell surface.

BCMA is a receptor for two ligands of the TNF superfamily: the B lymphocyte stimulator (mainly known as BlyS but described in the literature under various different names, including THANK, BAFF, B cell activator factor, TALL-1 and zTNF4); and APRIL (a proliferation-inducing ligand) [Hatzoglou et al. 2000 (PDF); Shu et al. 2000 (PDF); Gross et al. 2000 (PDF); Yu et al. 2000 (PDF); Marsters et al. 2000 (PAP)]. The coordinate binding of BLyS to BCMA and TACI (a distinct receptor: "transmembrane activator and CAML-interactor") activates transcription factor NF-κB and increases expression of Bcl-2 that inhibits apoptosis. This combined action promotes B cell differentiation, proliferation and survival.

In this regard, BCMA is involved in the survival of long-lived bone marrow plasma cells [O'Connor et al. 2004 (PDF)], which negatively affects autoimmune diseases. Furthermore, on the basis of transgenic mouse experiments, it was suggested that BCMA might be involved in autoimmune diseases, such as lupus erythematosus (SLE) [Gross et al. 2000; Mackay et al. 1999; Khare et al. 2000]. BCMA is also involved in the development of humoral immunity (e.g., antibody production) and additional reports disclose a role for BCMA in various immune-related disorders (such as IBD or multiple sclerosis) as well as in cancers (for a complete review of the BCMA/BLyS system, please see Mackay et al. 2004). In this respect, various antagonists of BCMA have been proposed in the literature, for use in the treatment of immune diseases.

Such antagonists include antibodies against BCMA extracellular domain (e.g. WO02/66516) or soluble forms of BCMA, i.e., polypeptides comprising essentially the extracellular domain of BCMA and lacking an intracellular region. In this regard, several reports indicate that the isolated BCMA extracellular domain can be used therapeutically or in fusion proteins (WO00/40716, WO00/68378, WO01/60397, WO01/87977, WO03/35846, WO03/72713). Application number WO03/72713 provides methods and compositions for treating neurodegenerative immunological disorders in mammals by administering proteins comprising a soluble BCMA. The protein may include the full extracellular domain (residues 1-50), the CRD region (residues 8-41) or other generic smaller variants. BCMA-IgG fusion proteins have also been disclosed in the literature, having therapeutic properties against autoimmune diseases or cancers [Rennert et al. 2000; Yu et al. 2000; Pelletier et al. 2003]. Also, the ligand-binding domain of BCMA has been studied by mutagenesis, giving rise to variants thereof with different affinity/specificity, that have used fusion proteins [Patel et al. 2004]. Deletion variants of BCMA intracellular region are also disclosed in Hatzoglou et al. 2000.

BCMA thus represents a recognized target for the treatment of various pathological conditions in human subjects, and the development of effective antagonist or alternative BCMA polypeptides would be of high value for the pharmaceutical industry.

SUMMARY OF THE PRESENT INVENTION

The present invention discloses novel BCMA polypeptide variants and their uses, particularly for therapeutic or prophylactic treatment in human subjects. The invention also discloses nucleic acids encoding said polypeptides, vectors comprising such nucleic acids, in particular, expression vectors, and recombinant cells containing the same, as well as corresponding pharmaceutical compositions. The invention further discloses methods of producing such polypeptides and methods and tools for detecting or dosing these polypeptides in any sample. Further included are antibodies specific for the novel BCMA polypeptide variants of the present invention.

More particularly, the invention results from the identification, isolation and characterization of a naturally-occurring, novel splicing variant of human BCMA, having particular structural and biological properties, which represents a valuable pharmaceutical product.

An object of this invention thus resides in isolated BCMA polypeptide variants, or a distinctive fragment thereof. The polypeptide variants of this invention comprise the sequence of a ligand-binding domain and a NF-κB activation domain of a BCMA polypeptide, and lack a functional trans-membrane domain. BCMA polypeptides of this invention represent soluble forms of BCMA, which may be used as antagonists thereof in various pathological conditions.

Another object of this invention resides in a fusion protein comprising a BCMA polypeptide variant as defined above.

Another object of this invention resides in a conjugate comprising a BCMA polypeptide variant as defined above.

Another object of this invention resides in a receptor complex comprising a BCMA polypeptide variant as defined above.

A further object of this invention resides in a nucleic acid encoding a BCMA polypeptide variant or a fusion protein as defined above, as well as any cloning or expression vector comprising such a nucleic acid.

The invention also relates to recombinant host cells comprising a vector or nucleic acid as defined above, as well as to methods of producing a BCMA polypeptide variant as defined above using such recombinant cells.

A further aspect of this invention resides in a pharmaceutical composition comprising a product (e.g., a polypeptide, fusion protein, conjugate, receptor complex, nucleic acid, vector or recombinant cell) as defined above.

A further aspect of this invention resides in the use of a product (e.g., a polypeptide, fusion protein, conjugate, receptor complex, nucleic acid, vector or recombinant cell) as defined above, for the manufacture of a pharmaceutical composition for use in a human subject.

The above products and pharmaceutical composition are particularly suited, for instance, for treating immune-related disorders or cancers, in particular for treating autoimmune diseases (e.g., multiple sclerosis, rheumatoid arthritis, systemic lupus, IBD, encephalomyelitis, myasthenia gravis, etc.), inflammatory diseases (e.g., joint pain, septic shock, CNS inflammation), allergy, asthma, bronchitis, emphysema, renal diseases, diabetes, cancers, as well as any B-cell-mediated disorder.

A further object of this invention also relates to an antibody, or a fragment or derivative of such an antibody that selectively binds a polypeptide as defined above.

A further aspect of this invention resides in a method of detecting or dosing a polypeptide as defined above in a sample, e.g., using an antibody, fragment or derivative thereof as defined above.

Other aspects of this invention include primers and probes specific for a nucleic acid as defined above, as well as their uses to detect or diagnose the presence of such a nucleic acid in a sample.

LEGEND TO THE FIGURES

FIG. 1: Genomic organization of a human BCMA variant of this invention.

FIG. 2: Sequence alignments between mature BCMA and a BCMA variant of this invention.

Figure 3:
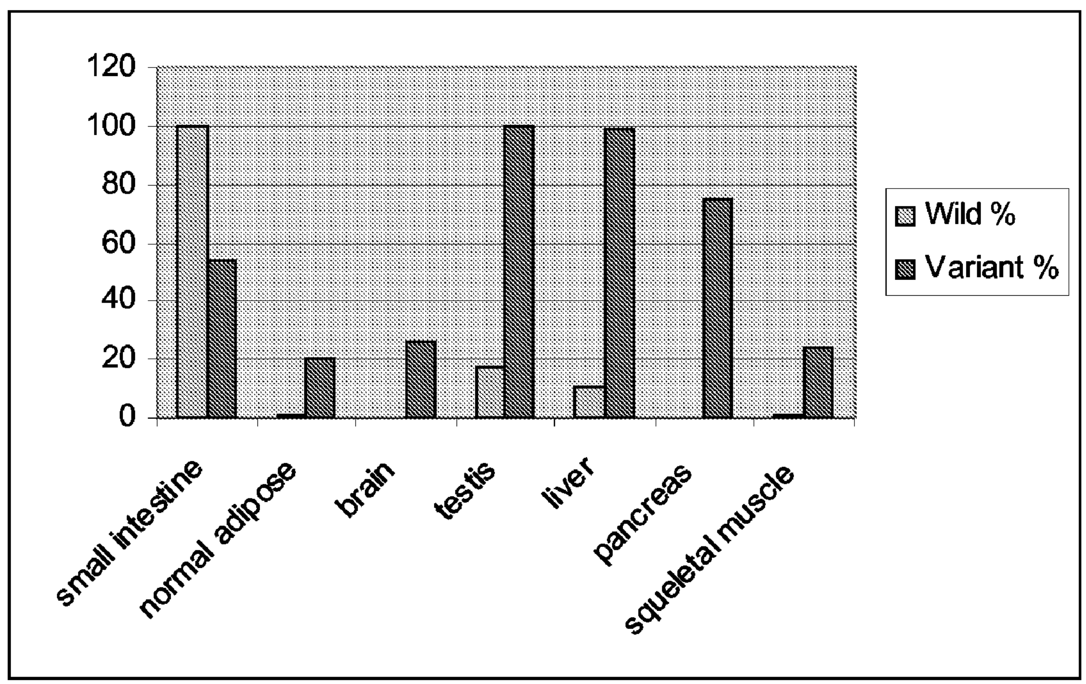

FIG. 3: Tissue expression of a BCMA variant of this invention.

DETAILED DESCRIPTION OF THE INVENTION

The present invention results from the identification and characterization of novel biologically active human BCMA polypeptide variants. These polypeptides typically comprise the sequence of a mature human BCMA polypeptide that lacks a functional trans-membrane domain. Further included are distinctive fragment which retain the biological activity of BCMA polypeptide variants of the present invention. The present invention may be naturally occurring or synthetic BCMA polypeptide variants and represent valuable therapeutic molecules. Furthermore, due to the absence of a functional trans-membrane domain, BCMA polypeptide variants of this invention are not anchored into a cell membrane, and may circulate within biological fluids, particularly blood, plasma, serum, lymph or the like. Such soluble BCMA polypeptide variants represent decoys that can bind natural, endogenous ligands of BCMA (e.g., BAFF or APRIL), thereby reducing BCMA-mediated activities. Soluble BCMA polypeptide variants of this invention represent natural antagonists of BCMA and may be used as such, or in the form of, e.g., a fusion protein, conjugate or receptor complex, for treating disorders related to B-cell function, in particular immune related disorders or cancers.

A particular object of this invention residues in isolated BCMA polypeptide variants, or a distinctive fragment thereof, wherein said polypeptide variants comprise a sequence of a ligand-binding domain and a NF-κB activation domain, and lack a functional trans-membrane domain, yet retain BCMA antagonist activity.

Within the context of the present invention, BCMA designates a B Cell Maturation Antigen as disclosed for instance in Laabi et al. 1992 or Madry et al. 1998. The sequence of a human BCMA protein is available at Swissprot under Accession number Q02223. A specific example of a human BCMA protein is provided in SEQ ID NO: 1 [human TR17]. It should be understood that the term BCMA also includes functional equivalents of the above sequence, i.e., naturally-occurring polymorphisms, sequences originating from other species, as well as sequences comprising one or more amino acid modification(s) that do(es) not substantially affect BCMA protein function. Functional equivalents typically exhibit 80, 85, 90, 91, 92, 93, 94, 95, 96, 97, 98 or 99% sequence identity with SEQ ID NO: 1.

As mentioned above, the BCMA polypeptide variants of this invention comprise a functional ligand-binding domain and NF-κB activation domain, but lack a functional trans-membrane domain. The invention shows that such proteins are produced naturally, and represent unexpected BCMA variants with unusual structural conformation. Indeed, in contrast to conventional soluble forms of a receptor, which retain an extra-cellular portion of the receptor, the molecules of the present invention retain functional intracellular residues, particularly a NF-κB activation domain.

BCMA polypeptide variants of this invention comprise an amino acid sequence derived from the ligand-binding domain of BCMA, as well as a sequence derived from the NF-κB activation domain of BCMA.

The sequence derived from the ligand-binding domain of BCMA may be derived from or comprise the sequence of all or a ligand-binding part of the extra-cellular domain of BCMA, or a functional equivalent thereof. Preferably, the sequence comprises amino acid residues 8-41 of SEQ ID NO: 1, even more preferably, amino acid residues 7-41 or 1-43 of SEQ ID NO: 1, or a functional equivalent thereof. As mentioned above, a functional equivalent designates any modified sequence comprising one or more amino acid deletion, addition and/or substitution, that retains the ability to bind a BCMA ligand.

A particular object of this invention relates to an isolated BCMA polypeptide variant as defined above, comprising amino acid residues 7-41 of SEQ ID NO: 1, preferably amino acid residues 1-43 of SEQ ID NO: 1.

The sequence derived from the NF-κB activation domain of BCMA may be derived from or comprise the sequence of all or a NF-κB activation part of the intra-cellular domain of BCMA, or a functional equivalent thereof. Preferably, the sequence comprises amino acid residues 119-143 of SEQ ID NO: 1, even more preferably, amino acid residues 94-184 of SEQ ID NO: 1, or a functional equivalent thereof. As mentioned above, a functional equivalent designates any modified sequence comprising one or more amino acid deletions, additions and/or substitutions, that retain the ability to activate NF-κB.

A particular object of this invention relates to an isolated BCMA polypeptide variant as defined above, wherein said polypeptide comprises amino acid residues 119-143 of SEQ ID NO: 1, preferably amino acid residues 94-184 of SEQ ID NO: 1.

The BCMA polypeptide variants of this invention lack a functional trans-membrane domain, i.e., they do not contain a BCMA-derived functional domain allowing membrane-anchoring of the polypeptide. The absence of a functional trans-membrane domain may result from any amino acid alteration (e.g., deletion, substitution and/or addition of one or several amino acid residues) in a BCMA trans-membrane domain resulting in a non-functional trans-membrane domain. In a typical embodiment, the lack of a functional trans-membrane domain results from a deletion of all or part of the amino acid residues forming the trans-membrane domain, preferably a deletion of amino acid residues 55-77 of SEQ ID NO: 1, more preferably of amino acid residues 44-93 of SEQ ID NO: 1.

The BCMA polypeptide variants of this invention preferably have at least one biological activity. In particular, such biological activity may include:

the ability to compete with BCMA for APRIL the ability to reduce the number of circulating B-cells in normal mice the ability to reduce the tumor volume in athymic mice models.

Such biological activity may determined by any suitable assay known the skilled person, in particular, the above activities can be measured by the assays further described in Example C hereinbelow.

In one embodiment BCMA polypeptide variants of this invention preferably antagonize at least one biological activity of BCMA and/or APRIL and/or BAFF in vitro or in vivo.

Assays by which BCMA activity may be identified appear in the references WO 99/00518 (Jun. 26, 1997); WO99/11791 (Sep. 5, 1997); WO 99/12965 (Sep. 12, 1997); EP911 633 (Oct. 8, 1997); EP 919 620 (Nov. 26, 1997); WO 99/28462 (Dec. 3, 1997); WO99/33980 (Dec. 30, 1997); WO 99/35170 (Jan. 5, 1998); Hahne et al. (1998) L Exp. Med. 188: 1185-90; WO98/18921 (May 7, 1998); WO 98/27114 (Jun. 25, 1998); EP869 180 (Oct. 7, 1998); WO 98/55620 and WO 98/55621 (Dec. 10, 1998); WO 99/11791 (Mar. 11, 1999); WO99/12964 (Mar. 18, 1999); and Gross et al. (2000), Nature 404: 995-9. Any of the assays described therein and herein may be modified as needed by methods known to persons having ordinary skill in the art.

A particular object of this invention relates to an isolated BCMA polypeptide variant as defined above, wherein said polypeptide comprises a deletion of amino acid residues 55-77 of SEQ ID NO: 1, preferably amino acid residues 44-93 of SEQ ID NO: 1. Furthermore, the BCMA polypeptide may comprise one or several additional amino acid residues between the ligand-binding and NF-κB activation domains, which may result from cloning or natural splicing process. As an example, the polypeptide may comprise an additional Arginine residue.

A specific embodiment of this invention is a BCMA polypeptide variant having or comprising SEQ ID NO: 3 [BCMA_short], a functional equivalent thereof or a distinctive fragment thereof, that retain BCMA antagonist activity The present invention also includes any polypeptide comprising a distinctive fragment of a BCMA polypeptide variant as disclosed above. Within the context of this invention, a distinctive fragment designates a fragment of at least 5 consecutive amino acids that comprises a junction sequence formed as a result of the deleted intervening amino acid residues. Such a distinctive fragment may comprise up to 10, 20, 30, 40, 50 or more consecutive amino acid residues of the variant, as long as it comprises the above defined junction sequence. The junction sequence may comprise 5, 6, 7, 8, 9, 10 or more consecutive amino acid residues formed as a result of the deleted intervening amino acid residues. Preferably a distinctive fragment also comprises the ligand-binding domain. Additionally, a distinctive fragment may also comprise the NF-kappa B activation domain. Preferably, distinctive fragments are soluble. Preferably, distinctive fragments retain binding activity for BAFF and/or APRIL.

A particular object of this invention thus resides in an isolated polypeptide which comprises the amino acid sequence NARSG (residues 42-46 of SEQ ID NO: 3) or CNARSGL (residues 41-47 of SEQ ID NO: 3).

Preferred BCMA polypeptide variants of the present invention are soluble, i.e., they do not contain a functional membrane-anchoring sequence and may thus circulate within body fluids. Also, preferred BCMA polypeptide variants of this invention retain the ability to bind BCMA natural ligands, such as BAFF and/or APRIL. Such polypeptides thus function as antagonists and may be used to inhibit BCMA-mediated activities in, e.g., pathological conditions.

The present invention also relates to fusion proteins comprising a BCMA polypeptide as disclosed above, operably linked to an additional amino acid domain. The additional amino acid domain may be located upstream (N-ter) or downstream (C-ter) from the sequence of the BCMA polypeptide. The additional domain may comprise any functional region, providing for instance an increased stability, targeting or bioavailability of the fusion protein; facilitating purification or production, or conferring on the molecule additional biological activity. Typical examples of such additional amino acid domains include, without limitation, a tag, a targeting peptide, a constant region of an immunoglobulin, a multimerization domain and/or a biologically active protein or fragment thereof or a heterodimeric protein hormone such as human chorionic gonadotropin (hCG) as described in U.S. Pat. No. 6,193,972. The term "operably linked" indicates that the polypeptide and additional amino acid domain are associated through peptide linkage, either directly or via spacer residues (e.g. one or more Gly-Ser motifs). In this manner, the fusion protein can be produced recombinantly, by direct expression in a host cell of a nucleic acid molecule encoding the same, as will be discussed below. Also, if needed, the additional amino acid sequence included in the fusion proteins may be eliminated, either at the end of the production/purification process or in vivo, e.g., by means of an appropriate endo-/exopeptidase. For example, a spacer sequence included in the fusion protein may comprise a recognition site for an endopeptidase (such as a caspase) that can be used to separate by enzymatic cleavage the desired polypeptide variant from the additional amino acid domain, either in vivo or in vitro.

Specific examples of the additional amino acid residues include a tag sequence selected e.g., from a GST sequence and a His tag sequence. The tag sequence may be linked to the C-terminus or to the N-terminus of the BCMA polypeptide variant, preferably to the C-terminus.

In a particular embodiment, the additional amino acid residues function as a peptide signal directing secretion of the protein. BCMA is a Type III transmembrane protein which does not contain a particular signal peptide (the same sequence acts as both transmembrane and signal sequence). BCMA polypeptide variants of this invention may however be fused to a heterologous signal sequence, at the N-terminus of the polypeptide), to allow or increase secretion thereof. Such a signal peptide may be any sequence functional in a selected host cell, such as a eukaryotic (e.g., mammalian) or prokaryotic host cell. Examples of such peptide signals are well known in the art.

In a further particular embodiment, the additional amino acid residues in the fusion protein comprise an amino acid sequence derived from the constant region of an immunoglobulin, particularly the Fc portion of a human immunoglobulin. The sequence of the Fc portion may be derived for instance from an IgG, preferably from a human IgG. Said Ig sequence may also be modified to reduce effector function or to increase the stability of a resulting dimer. The amino acid sequence derived from the constant region of an immunoglobulin may be linked to the C-terminus or to the N-terminus of the BCMA polypeptide variant, preferably to the C-terminus.

In a further particular embodiment, the additional amino acid residues in the fusion protein comprise a multimerization domain, allowing complexes to be formed between two or more fusion proteins of this invention, or between one or more fusion proteins of this invention and a distinct protein. An example of such multimerization domains include a leucine zipper. The multimerization domain may be linked to the C-terminus or to the N-terminus of the BCMA polypeptide variant, preferably to the C-terminus.

It should be understood that fusion proteins of this invention may comprise either only one of the above additional amino acid residues, or a combination thereof. For instance, a fusion protein may comprise a signal peptide and a tag sequence, or a signal peptide and a multimerization domain or a signal peptide and the constant region of an immunoglobulin, or a tag and the constant region of an immunoglobulin. Also, as indicated above, some of the additional amino acid sequences may be linked to the BCMA polypeptide variant through spacer residues, particularly through cleavable spacer residues allowing subsequent separation of these elements, if needed. Such fusion proteins may be produced by any conventional technique known per se in the art, as will be discussed below.

The polypeptides or fusion proteins of the invention can be in isolated form or in the form of active conjugates or complexes thereof.

In this regard, a particular object of this invention resides in a conjugate comprising a BCMA polypeptide variant or a fusion protein as defined above. The conjugate comprises at least one chemical group (covalently) coupled to the polypeptide, such as a label, stabilizer, toxin, drug, etc. In a particular embodiment, the conjugate comprises a molecule selected from radioactive labels, biotin, fluorescent labels, cytotoxic agents, drugs or drug delivery agents, covalently coupled to any amino acid residue of the BCMA polypeptide variant. Useful conjugates can be generated using molecules and methods known per se in the art, for example for allowing the detection of the interaction with a ligand (radioactive or fluorescent labels, biotin), or improving the agents in terms of drug delivery efficacy, such as polyethylene glycol and other natural or synthetic polymers (Harris J M and Chess R B, 2003; Greenwald R B et al., 2003; Pillai O and Panchagnula R, 2001).

An other aspect of this invention is a receptor complex comprising a BCMA polypeptide variant or a fusion protein or a conjugate as defined above. Such receptor complexes typically comprise a multimer formed between two or more fusion proteins of this invention, or between one or more fusion proteins of this invention and a distinct protein. Multimerization may be obtained through particular multimerization domain(s) contained in the proteins, as discussed supra. Such multimers may be formed in vitro, or they may form in vivo, upon administration to an organism.

Polypeptides and fusion proteins of this invention may be produced by any technique known per se in the art, such as by recombinant technologies, chemical synthesis, cloning, ligations, or combinations thereof.

In a particular embodiment, the polypeptides or fusion proteins are produced by recombinant technologies, e.g., by expression of a corresponding nucleic acid in a suitable host cell.

In this regard, the term "nucleic acid molecule" encompasses any nucleic acid molecule encoding a polypeptide or fusion protein as disclosed above. The nucleic acid may be a DNA (e.g., cDNA, gDNA, synthetic DNA, etc.), a RNA (e.g., mRNA), a PNA (peptide nucleic acid), etc., more preferably a DNA, even more preferably a cDNA molecule. A particular object of this invention resides more specifically in a nucleic acid molecule which comprises a nucleotide sequence selected from SEQ ID NO: 2, or a complementary strand or degenerate sequence thereof.

A degenerate sequence designates any nucleotide sequence encoding the same amino acid sequence as a reference nucleotide sequence, but comprising a distinct nucleotide sequence as a result of the genetic code degeneracy.

A further object of this invention is a vector comprising a nucleic acid molecule as defined above. The vector may be any cloning or expression vector, integrative or autonomously replicating, functional in any prokaryotic or eukaryotic cell. In particular, the vector may be a plasmid, cosmid, virus, phage, episome, artificial chromosome, and the like. The vector may comprise regulatory elements, such as a promoter, terminator, enhancer, selection marker, origin of replication, etc. Specific examples of such vectors include prokaryotic plasmids, such as pBR, pUC or pcDNA plasmids; viral vectors, including retroviral, adenoviral or AAV vectors; bacteriophages; baculoviruses; BAC or YAC, etc., as will be discussed below A further aspect of this invention is a recombinant host cell, wherein said cell comprises a nucleic acid molecule or a vector as defined above. The host cell may be a prokaryotic or eukaryotic cell. Examples of prokaryotic cells include bacteria, such as *E. coli*. Examples of eukaryotic cells are yeast cells, plant cells, mammalian cells, including any primary cell culture or established cell line (e.g., 3T3, Vero, HEK293, TN5, etc.). Particularly preferred mammalian cells of the present invention are CHO cells.

An other object of this invention is a method of producing a BCMA polypeptide variant or fusion protein as defined above, the method comprising culturing a recombinant host cell of the invention under conditions allowing expression of the nucleic acid molecule, and recovering the polypeptide produced. The polypeptide may be recovered from the cell culture supernatant, if the polypeptide is secreted, or from the cell cytoplasm or debris, if suitable. The polypeptide product may be glycosylated or not, or contain other post-translational modifications depending on the host cell used.

Many books and reviews provide teachings on how to clone and produce recombinant proteins using vectors and prokaryotic or eukaryotic host cells, such as some titles in the series "A Practical Approach" published by Oxford University Press ("DNA Cloning 2: Expression Systems", 1995; "DNA Cloning 4: Mammalian Systems", 1996; "Protein Expression", 1999; "Protein Purification Techniques", 2001).

In general, the vectors can be episomal or non-/homologously integrating vectors, which can be introduced in the appropriate host cells by any suitable means (transformation, transfection, conjugation, protoplast fusion, electroporation, calcium phosphate-precipitation, direct microinjection, etc.) to transform them. Factors of importance in selecting a particular plasmid, viral or retroviral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species. The vectors should allow the expression of the polypeptide or fusion proteins of the invention in prokaryotic or eukaryotic host cells, under the control of appropriate transcriptional initiation/termination regulatory sequences, which are chosen to be constitutively active or inducible in said cell. A cell line substantially enriched in such cells can be then isolated to provide a stable cell line.

A particularly preferred method of high-yield production of a recombinant polypeptide of the present invention is through the use of dihydrofolate reductase (DHFR) amplification in DHFR-deficient CHO cells, by the use of successively increasing levels of methotrexate as described in U.S. Pat. No. 4,889,803. The polypeptide obtained may be in a glycosylated form.

For eukaryotic host cells (e.g. yeasts, insect or mammalian cells), different transcriptional and translational regulatory sequences may be employed, depending on the nature of the host. They may be derived form viral sources, such as adenovirus, papilloma virus, Simian virus or the like, where the regulatory signals are associated with a particular gene which has a high level of expression. Examples are the TK promoter of the Herpes virus, the SV40 early promoter, the yeast gal4 gene promoter, etc. Transcriptional initiation regulatory signals may be selected which allow for repression and activation, so that expression of the genes can be modulated. The cells which have been stably transformed by the introduced DNA can be selected by also introducing one or more markers which allow for selection of host cells which contain the expression vector. The marker may also provide for phototrophy to an auxotrophic host, biocide resistance, e.g. antibiotics, or heavy metals such as copper, or the like. The selectable marker gene can be either directly linked to the DNA sequences to be expressed (e.g., on the same vector), or introduced into the same cell by co-transfection. Additional elements may also be needed for optimal synthesis of proteins of the invention.

Particularly suitable prokaryotic cells include bacteria (such as *Bacillus subtilis* or *E. coli*) transformed with a recombinant bacteriophage, plasmid or cosmid DNA expression vector. Such cells typically produce proteins comprising a N-terminal Methionine residue, such proteins representing particular objects of this invention. Preferred cells to be used in the present invention are eukaryotic host cells, e.g. mammalian cells, such as human, monkey, mouse, and Chinese Hamster Ovary (CHO) cells, because they provide post-translational modifications to protein molecules, including correct folding or glycosylation at correct sites. Alternative eukaryotic host cells are yeast cells (e.g., *Saccharomyces, Kluyveromyces*, etc.) transformed with yeast expression vectors. Also yeast cells can carry out post-translational peptide modifications including glycosylation. A number of recombinant DNA strategies exist which utilize strong promoter sequences and high copy number of plasmids that can be utilized for production of the desired proteins in yeast. Yeast cells recognize leader sequences in cloned mammalian gene products and secrete polypeptides bearing leader sequences (i.e., prepeptides).

For long-term, high-yield production of a recombinant polypeptide, stable expression is preferred. For example, cell lines which stably express the polypeptide of interest may be transformed using expression vectors which may contain viral origins of replication and/or endogenous expression elements and a selectable marker gene on the same or on a separate vector. Following the introduction of the vector, cells may be allowed to grow for 1-2 days in an enriched media before they are switched to selective media. The purpose of the selectable marker is to confer resistance to selection, and its presence allows growth and recovery of cells that successfully express the introduced sequences. Resistant clones of stably transformed cells may be proliferated using tissue culture techniques appropriate to the cell type. A cell line substantially enriched in such cells can be then isolated to provide a stable cell line.

Mammalian cell lines available as hosts for expression are known in the art and include many immortalised cell lines available from the American Type Culture Collection (ATCC) including, but not limited to, Chinese hamster ovary (CHO), HeLa, baby hamster kidney (BHK), monkey kidney (COS), C127, 3T3, BHK, HEK 293, Bowes melanoma and human hepatocellular carcinoma (for example Hep G2) cells and a number of other cell lines. In the baculovirus system, the materials for baculovirus/insect cell expression systems are commercially available in kit form from, inter alia, Invitrogen.

In addition to recombinant DNA technologies, the polypeptides or fusion proteins of this invention may be prepared by chemical synthesis technologies. Examples of chemical synthesis technologies are solid phase synthesis and liquid phase synthesis. As a solid phase synthesis, for example, the amino acid corresponding to the carboxy-terminus of the polypeptide to be synthesised is bound to a support which is insoluble in organic solvents and, by alternate repetition of reactions (e.g., by sequential condensation of amino acids with their amino groups and side chain functional groups protected with appropriate protective groups), the polypeptide chain is extended. Solid phase synthesis methods are largely classified by the tBoc method and the Fmoc method, depending on the type of protective group used. Totally synthetic proteins of size comparable to that of BCMA are disclosed in the literature (Brown A et al., 1996).

The polypeptides of the present invention can be produced, formulated, administered, or generically used in other alternative forms that can be preferred according to the desired method of use and/or production. The proteins of the invention can be post-translationally modified, for example by glycosylation. The polypeptides or proteins of the invention can be provided in isolated (or purified) active form, or as precursors, derivatives and/or salts thereof.

As indicated above, the term "active" or "biologically active" means that such polypeptides have the capacity to bind a BCMA ligand and function as a BCMA antagonist.

"Precursors" are compounds which can be converted into the polypeptides of present invention by metabolic and/or enzymatic processing prior to or after administration thereof to cells or an organism.

The term "salts" herein refers to both salts of carboxyl groups and to acid addition salts of amino groups of the polypeptides of the present invention. Salts of a carboxyl group may be formed by means known in the art and include inorganic salts, for example, sodium, calcium, ammonium, ferric or zinc salts, and the like, and salts with organic bases as those formed, for example, with amines, such as triethanolamine, arginine or lysine, piperidine, procaine and the like. Acid addition salts include, for example, salts with mineral acids such as, for example, hydrochloric acid or sulfuric acid, and salts with organic acids such as, for example, acetic acid or oxalic acid. Any of such salts should have substantially similar activity to the polypeptides of the invention.

The term "derivatives" as used herein refers to derivatives that can be prepared from the functional groups present on the lateral chains of the amino acid moieties or on the amino-/or carboxy-terminal groups according to methods known per se in the art. Such derivatives include for example esters or aliphatic amides of the carboxyl-groups and N-acyl derivatives of free amino groups or O-acyl derivatives of free hydroxyl-groups and are formed with acyl-groups as for example alcanoyl- or aroyl-groups.

Purification of the polypeptides or fusion proteins of the invention can be carried out by a variety of methods known per se in the art, such as, without limitation, any conventional procedure involving extraction, precipitation, chromatography, electrophoresis, or the like. A particular purification procedure is affinity chromatography, using (monoclonal) antibodies or affinity groups which selectively bind the polypeptide and which are typically immobilized on a gel matrix contained within a column. Purified preparations of the proteins of the invention, as used herein, refers to preparations which contain less than 15% of contaminants, more preferably which comprise at least 90, 95 or 97% of the polypeptide. An isolated protein, polypeptide or nucleic acid denotes a protein, polypeptide or nucleic acid which is not in its natural environment.

A further object of this invention is a pharmaceutical composition comprising a product (e.g., a polypeptide, fusion protein, conjugate, receptor complex, nucleic acid molecule, vector or cell) as defined above, and a pharmaceutically acceptable carrier or diluent. More preferred pharmaceutical compositions of this invention comprise a polypeptide comprising SEQ ID NO: 3, or a fusion protein comprising such a polypeptide.

An other aspect of this invention relates to the use of a product (e.g., a polypeptide, fusion protein, conjugate, receptor complex, nucleic acid molecule, vector or cell) as disclosed above, for the manufacture of a pharmaceutical composition for treating a human subject.

The above products and pharmaceutical composition are particularly suited, for instance, for treating immune-related disorders or cancers, in particular for treating autoimmune diseases (e.g., multiple sclerosis, rheumatoid arthritis, systemic lupus, IBD, encephalomyelitis, myasthenia gravis, etc.), inflammatory diseases (e.g., joint pain, septic shock, CNS inflammation), allergy, asthma, bronchitis, emphysema, renal diseases, diabetes, cancers, as well as any B-cell-mediated disorder.

In this regard, a particular object of the invention relates to the use of a product as defined above for the manufacture of a pharmaceutical composition for treating an immune disorder or a cancer in a subject.

A further particular object of the invention relates to the use of a product as defined above for the manufacture of a pharmaceutical composition for treating an inflammatory disorder in a subject.

A further particular object of the invention relates to the use of a product as defined above for the manufacture of a pharmaceutical composition for treating allergy, asthma, bronchitis or emphysema in a subject.

A further particular object of the invention relates to the use of a product as defined above for the manufacture of a pharmaceutical composition for inhibiting or reducing antibody production in a subject, particularly for reducing auto-antibody production in a subject having an auto-immune disease.

The invention also relates to corresponding methods of treatment using a product as defined above. In particular, an object of this invention is a method of treating a cancer, an auto-immune disease or an inflammatory disease in a subject, comprising administering to a subject in need thereof an effective amount of a product as defined above.

Another particular use of this invention is for inhibiting B-cell maturation or proliferation in a subject, particularly in a subject having an immune related disorder or an inflammatory disease.

The invention also encompasses a method of reducing the interaction between BCMA and a ligand thereof in a subject, the method comprising administering to the subject an effective amount of a product as defined above.

Within the context of the present invention, the term treatment includes preventive or curative treatments in a subject, particularly a human subject. Treatment includes any amelioration of a clinical manifestation of a disease, delaying the onset of a disease, particularly the onset of an acute disease; reducing its severity, reducing progression of the disease or suppressing the cause(s) thereof, such as reducing (auto)antibody production, reducing B-cell proliferation, and the like.

Effective doses may be adjusted by the skilled artisan, depending on the patient, disease and product. Typically, effective doses are comprises between about 5 μg/kg and 50 mg/kg, particularly between 100 μg/kg and 10 mg/kg.

The pharmaceutical compositions may contain one or more product(s) of this invention, either as the sole active ingredient or for use in combination with other active ingredient, and any suitable pharmaceutically acceptable diluents, carriers, biologically compatible vehicles and additives which are suitable for administration to an animal (for example, physiological saline solution) and optionally comprising auxiliaries (like excipients, stabilizers, or adjuvants) which facilitate the processing of the active compounds into preparations which can be used pharmaceutically. The pharmaceutical compositions may be formulated in any acceptable way to meet the needs of the mode of administration. For example, the use of biomaterials and other polymers for drug delivery, as well the different techniques and models to validate a specific mode of administration, are disclosed in literature (Luo B and Prestwich G D, 2001; Cleland J L et al., 2001).

"Pharmaceutically acceptable" is meant to encompass any carrier, which does not interfere with the effectiveness of the biological activity of the active ingredient and that is not toxic to the host to which is administered. For example, for parenteral administration, the above active ingredients may be formulated in unit dosage form for injection in vehicles such as saline, dextrose solution, serum albumin and Ringer's solution. Carriers can be selected also from starch, cellulose, talc, glucose, lactose, sucrose, gelatin, malt, rice, flour, chalk, silica gel, magnesium stearate, sodium stearate, glycerol monostearate, sodium chloride, dried skim milk, glycerol, propylene glycol, water, ethanol, and the various oils, including those of petroleum, animal, vegetable or synthetic origin (peanut oil, soybean oil, mineral oil, sesame oil).

Any accepted mode of administration can be used and determined by those skilled in the art to establish the desired blood levels of the active ingredients. For example, administration may be by various parenteral routes such as subcutaneous, intravenous, intradermal, intramuscular, intraperitoneal, intranasal, transdermal, rectal, oral, or buccal routes. The pharmaceutical compositions of the present invention can also be administered in sustained or controlled release dosage forms, including depot injections, osmotic pumps, and the like, for the prolonged administration of the polypeptide at a predetermined rate, preferably in unit dosage forms suitable for single administration of precise dosages.

Parenteral administration can be by bolus injection or by gradual perfusion over time. Preparations for parenteral administration include sterile aqueous or non-aqueous solutions, suspensions, and emulsions, which may contain auxiliary agents or excipients known in the art, and can be prepared according to routine methods. In addition, suspension of the active compounds as appropriate oily injection suspensions may be administered. Suitable lipophilic solvents or vehicles include fatty oils, for example, sesame oil, or synthetic fatty acid esters, for example, sesame oil, or synthetic fatty acid esters, for example, ethyl oleate or triglycerides. Aqueous injection suspensions that may contain substances increasing the viscosity of the suspension include, for example, sodium carboxymethyl cellulose, sorbitol, and/or dextran. Optionally, the suspension may also contain stabilizers. Pharmaceutical compositions include suitable solutions for administration by injection, and contain from about 0.01 to 99.99 percent, preferably from about 20 to 75 percent of active compound together with the excipient.

It is understood that the dosage administered will be dependent upon the age, sex, health, and weight of the recipient, kind of concurrent treatment, if any, frequency of treatment, and the nature of the effect desired. The dosage will be tailored to the individual subject, as is understood and determinable by one of skill in the art. The total dose required for each treatment may be administered by multiple doses or in a single dose. The pharmaceutical composition of the present invention may be administered alone or in conjunction with other therapeutics directed to the condition, or directed to other symptoms of the condition. Usually a daily dosage of active ingredient is comprised between 0.01 to 100 milligrams per kilogram of body weight per day. Ordinarily 1 to 40 milligrams per kilogram per day given in divided doses or in sustained release form is effective to obtain the desired results. Second or subsequent administrations can be performed at a dosage, which is the same, less than, or greater than the initial or previous dose administered to the individual.

A further aspect of this invention relates to compositions and methods for detecting or dosing a polypeptide or nucleic acid of this invention in a sample. Such compositions include, for instance, any specific ligand of a polypeptide of this invention, such as an antibody, or a fragment or derivative thereof; or any specific nucleic acid probes or primers.

In this regard, a further object of this invention is an antibody, or a fragment or derivative thereof, that selectively binds a BCMA polypeptide variant as disclosed above. In a more specific embodiment, the antibody, fragment or derivative thereof selectively binds an epitope comprising, or comprised in, amino acid residues NARSG (residues 42-46 of SEQ ID NO: 3) or CNARSGL (residues 41-47 of SEQ ID NO: 3). The invention also relates to a pharmaceutical composition comprising an antibody, fragment or derivative thereof as defined above.

Within the context of this invention, the term "selective" binding indicates that the antibodies preferentially bind the target polypeptide or epitope, i.e., with a higher affinity than any binding to any other antigen or epitope. In other words, binding to the target polypeptide can be discriminated from non-specific binding to other antigens.

It is preferred that the antibodies (or a fragments or derivatives thereof) according to the present invention exhibit binding affinity (Ka) to the target polypeptide or epitope of $10^6$ $M^{-1}$ or greater, preferably $10^7$ $M^{-1}$ or greater, more preferably $10^8$ $M^{-1}$ or greater and most preferably $10^9$ $M^{-1}$ or greater. The binding affinity of an antibody can be readily determined by one of ordinary skill in the art, for example, by Scatchard analysis (Scatchard G., Ann NY Acad. Sci. 51: 660-672, 1949).

Antibodies of this invention may be monoclonal or polyclonal antibodies, or fragments or derivative thereof having substantially the same antigen specificity. The term fragment includes any binding portion of an antibody, such as Fab, F(ab')2, CDR domains, etc. Derivatives include human or humanized antibodies, polyfunctional antibodies, single-chain antibodies (e.g., ScFv), diabodies, monobodies etc. Methods for producing antibodies, fragments or derivatives thereof are well known in the art, including immunization of an animal and collection of serum (polyclonal) or spleen cells (to produce hybridomas by fusion with appropriate cell lines).

"Single-chain antibodies" are fragments of an antibody comprising the VH and VL domains of said antibody, wherein these domains are present in a single polypeptide chain. Preferably, the Fv polypeptide further comprises a polypeptide linker between the VH and VL domains which enables the single-chain antibody molecule to form the desired structure for antigen binding. For a review of single-chain antibody molecules, see, Pluckthun in The Pharmacology of Monoclonal Antibodies, Vol. 113, Rosenburg and Moore eds., Springer-Verlag, New York, pp. 269-315 (1994).

The term "diabodies" refers to small antibody fragments with two antigen-binding sites, which fragments comprise a heavy-chain variable domain (VH) connected to a light-chain variable domain (VL) in the same polypeptide chain (VH-VL). Preferably, by using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., Proc. Natl. Acad. Sci. USA, 90:6444-6448 (1993).

The term "monobodies" as used herein, refers to antigen binding molecules with a heavy chain variable domain and no light chain variable domain. A monobody can bind to an antigen in the absence of light chain and typically has three CDR regions designated CDRH1, CDRH2 and CDRH3. Monobodies include "camelid monobodies" obtained from a source animal of the camelid family, including animals with feet with two toes and leathery soles. Animals in the camelid family include camels, llamas, and alpacas. It has been reported that camels (*Camelus dromedaries* and *Camelus bactrianus*) often lack variable light chain domains when material from their serum is analyzed, suggesting that sufficient antibody specificity and affinity can be derived form VH domains (three CDR loops) alone. Monobodies also include modified VH from various animal sources, in particular mammals (for example mouse, rat, rabbit, horse, donkey, bovine or human), which can bind to an antigen in the absence of VL. Preferably, the VH is modified in positions at the VL interface to provide for binding of the VH to antigen in absence of the VL. Davies and Riechmann have for example demonstrated that "camelized monobodies" with high affinity (binding affinity (Ka) to the target polypeptide of $10^7$ $M^{-1}$ or greater) and high specificity can be generated (Davies & Riechmann, 1995, Biotechnology (NY), 13(5):475-9). Non-specific binding of the VH through its interface for the light chain variable domain (VL) was prevented through three mutations (G44E, L45R and W47G) in this interface. These mutations were introduced to mimic camelid antibody heavy chains naturally devoid of light chain partners.

Methods of producing polyclonal antibodies from various species, including rodents, primates and horses, have been described for instance in Vaitukaitis et al. (J Clin Endocrinol Metab. 33 (1971) p. 988). Briefly, the antigen is combined with an adjuvant (e.g., Freund's adjuvant) and administered to an animal, typically by sub-cutaneous injection. Repeated injections may be performed. Blood samples are collected and immunoglobulins or serum are separated.

Methods of producing monoclonal antibodies may be found, for instance, in Harlow et al (Antibodies: A laboratory Manual, CSH Press, 1988) or in Kohler et al (Nature 256 (1975) 495), incorporated therein by reference. Briefly, these methods comprise immunizing an animal with the antigen, subsequently recovering spleen cells and fusing these cells with immortalized cells, such as myeloma cells, to produce hybridomas. Hybrodimas producing the desired monoclonal antibodies can be selected by limit dilutions. Antibodies may also be produced by selection of combinatorial libraries of immunoglobulins, as disclosed for instance in Ward et al (Nature 341 (1989) 544).

The antibodies may be coupled to heterologous moieties, such as toxins, labels, drugs or other therapeutic agents, covalently or not, either directly or through the use of coupling agents or linkers.

Antibodies of this invention may be used for detecting, dosing, purifying or neutralizing BCMA polypeptide variant of this invention. In a particular aspect, the invention thus resides in a method of detecting or dosing a BCMA polypeptide variant as defined above in a sample, comprising contacting such a sample with an antibody, fragment or derivative thereof as disclosed above, and determining the formation or dosing the (relative) quantity of an immune complex. The sample may be for instance any biological fluid, such as blood, plasma, serum, etc., optionally diluted and/or treated. The antibody, fragment or derivative thereof may be in suspension or immobilized on a support. The presence or amount of immune complexes may be determined by any technique known per se in the art, e.g., by ELISA, RIA, etc., e.g., using reporter antibodies, labelled antibodies, etc.

Another aspect of this invention is a nucleic acid probe, wherein said probe selectively hybridizes to a nucleic acid as defined above or the complementary strand thereof. Probes denote a defined nucleic acid segment (or nucleotide analog segment, e.g., polynucleotide as defined herein) which can be used to identify a specific polynucleotide sequence present in samples, said nucleic acid segment comprising a nucleotide sequence complementary of the specific polynucleotide sequence to be identified. Probes of this invention typically comprise single-stranded nucleic acids of between 12 to 600 nucleotides in length, for instance of between 12 and 500, more preferably of between 15 and 400, typically of between 20 and 300. The sequence of the probes can be derived from the sequences of the BCMA polypeptide variant gene sequence. The probe may contain nucleotide substitutions and/or chemical modifications, e.g., to increase the stability of hybrids or to label the probe. Typical examples of labels include, without limitation, radioactivity, fluorescence, luminescence, etc.

A further aspect of this invention is a nucleic acid primer that can be used to amplify at least a distinctive fragment of a nucleic acid molecule encoding a BCMA polypeptide variant as defined above. A "primer" denotes a specific oligonucleotide sequence which is complementary to a target nucleotide sequence and used to hybridize to the target nucleotide sequence. A primer serves as an initiation point for nucleotide polymerization catalyzed by either DNA polymerase, RNA polymerase or reverse transcriptase. Typical primers of this invention are single-stranded nucleic acid molecules of about 6 to 50 nucleotides in length, more preferably of about 8 to about 40 nucleotides in length. The sequence of the primer can be derived directly from the sequence of the target nucleic acid molecule. Perfect complementarity between the primer sequence and the target gene is preferred, to ensure high specificity. However, certain mismatch may be tolerated.

Particular nucleic acid primers are able to specifically hybridize with a portion of the BCMA variant nucleic acid that either flanks or encodes a distinctive fragment of such polypeptides. Specific examples of primers of this invention are disclosed below:

```
                                            (SEQ ID NO:4)
BCMA_shortLF2:      GATCATGTTGCAGATGGCTGGGC

                                            (SEQ ID NO:5)
BCMA_shortLR1:      AGTGGCACTGCTCGAGTCGAAATG
```

A further aspect of this invention thus resides in the use of a primer or probe as disclosed above to detect or diagnose the presence of a nucleic acid encoding a BCMA polypeptide variant of this invention in a sample. The method can be carried out according to techniques well know in the art, such as by contacting a sample with a probe as defined above under conditions allowing hybridisation to occur, and determining the presence of a hybrid; or by contacting a sample with a primer as defined above under conditions allowing nucleic acid amplification, and determining the presence of an amplification product.

Further aspects and advantages of the present invention will be disclosed in the following examples, which should be considered as illustrative only, and do not limit the scope of this application.

EXAMPLES

A. Identification and Characterization of BCMA Variants

1. SMART cDNA Synthesis (Production of Pool)

A) First-Srand cDNA Synthesis

Kit N° 634914 Clontech

1—Mix preparation:
 0.5 μl RNA sample
 1 μl 3' SMART CDSPrimer II A (10 μM)
 1 μl SMART II A Oligonucleotide (10 μm)
 2.5 μl Deionized H2O
2—Mix contents and spin the tube briefly in a microcentrifuge
3—Incubate at 72° C. for 2 min
4—Cool the tube on ice for 2 min
5—Add the following to each reaction tube:
 2 μl 5× First-Strand Buffer
 1 μl DTT (20 mM)
 1 μl 50× dNTP (10 mM)
 1 μl PowerScript Reverse Transcriptase
6—Incubate the tubes at 42° C. for 1 hour
7—Add 190 μl of TE 1× (pH 7.5)
8—Incubate at 72° C. 7 min
9—Stock at −20° C.

2. Agilent Protocol

1—Mix composition (1 reaction) for first PCR
 24.4 μl of H2O
 1 μl of reverse Transcriptase Th (rTTH, ref.N808.0188 Perkin)
 15 μl of Buffer rTTH 3,3× (Perkin)
 0,4 μl of dNTP (25 mM; ref.10297-018 Invitrogene)
 1 μl of mix oligos PCR1 (10 μM)
 6 μl of SMART cDNA (0,4 ng/μl)
 2,2 μl of Mg(OAc)2

| 2 - First PCR cycles | | | |
|---|---|---|---|
| 94° C. | 5' | | 1 cycle |
| 94° C. | 40" | ) | 35 cycles |
| 62° C. | 40" | | |
| 67° C. | 2' | | |
| 72° C. | 10' | | 1 cycle |
| 10° C. | hold | | |

3—Mix composition (1 reaction) for second PCR
- 38,8 μl of $H_2O$
- 5 μl of Buffer Taq+ (10×)
- 0,4 μl of dNTP (25 mM) 10297-018 Invitrogene)
- 0,3 μl of Taq+precision (600 211 Sire)
- 1 μl of mix oligos PCR2 (10 μM)
- 2 μl of Product of First PCR
- 2,5 μl of DMSO (100%)

| 4 - Second PCR cycles | | | |
|---|---|---|---|
| 94° C. | 1' | | |
| 94° C. | 40" | ) | 3 cycles |
| 45° C. | 40" | | |
| 72° C. | 2' | | |
| 94° C. | 40" | ) | 30 cycles |
| 55° C. | 40" | | |
| 72° C. | 2' | | |
| 72° C. | 10' | | |
| 10° C. | hold | | |

These experiments led to the isolation of a short form of BCMA (splice variant) having 125aa. The human gene for BCMA has 3 exons with canonical splice sites [Laabi et al. 1994(PDF)]. The new variant (BCMA_short) retains only exon 1 and exon 3 (FIG. 1). As depicted on FIG. 2, the new protein lacks the transmembrane domain but retains the six-cysteine-rich domain (e.g. BCMA short: QCSQNEYFD-SLLHACIPCQLRCSSNTPPLTCQRYC (SEQ ID NO: 10)) and the fragment allowing the activation of NF-κB (e.g. BCMA_short: LEYTVEECTCEDCIKSKPKVDSDHC (SEQ ID NO: 11)).

B. Tissue Distribution of the BCMA Splice Variant

The tissue distribution BCMA_short was determined using RT-PCR analysis in a series of RNA libraries generated from human tissues purchased by either Clontech (human polyA RNA pancreas, cod. 636119; human polyA RNA skeletal muscle, cod. 636120; human polyA RNA small intestine, cod.636125; human polyA RNA testis, cod.636115; human polyA RNA liver, cod.636101; human polyA RNA brain, cod.636102), or Invitrogen (human total RNA, Normal adipose, lot A5040004) as described in "SMART cDNA synthesis" paragraph above.

The two consecutive PCR reactions were performed using the different cDNA template and either leading to DNA segment that were either of identical (control RT-PCR) or significantly different length (test RT-PCR), when comparing the product of the RT-PCR reactions including the specific variant and the normal form.

In the control reactions, the two PCR consecutive reactions were performed with the following couple primers:

```
PCR1:
                                        (SEQ ID NO:4)
BCMA_shortLF2      GATCATGTTGCAGATGGCTGGGC
```

-continued

```
                                        (SEQ ID NO:5)
BCMA_shortLR1      AGTGGCACTGCTCGAGTCGAAATG

PCR2:
                                        (SEQ ID NO:6)
Sc3179.F           TTCGCCACCATGTTGCAGATGGCTGG

                                        (SEQ ID NO:7)
Scsp(R1)           TGCCCAGGAGACCTGATCTTGCATT
```

The outcome of the reaction is a 157 bp band if either the normal or the short variant of BCMA is expressed in the RNA library.

In the test reactions, the two PCR consecutive reactions were performed with the following couple primers:

```
PCR1:
                                        (SEQ ID NO:4)
BCMA_shortLF2      GATCATGTTGCAGATGGCTGGGC

                                        (SEQ ID NO:5)
BCMA_shortLR1      AGTGGCACTGCTCGAGTCGAAATG

PCR2:
                                        (SEQ ID NO:6)
Sc3179.F           TTCGCCACCATGTTGCAGATGGCTGG

                                        (SEQ ID NO:7)
Sc3179.R           TCAATGGTGATGGTGATGGTGCCTAG
                   CAGAAATTGATTTCT
```

The outcome of the reaction is a 435 bp and/or a 582 bp if the BCMA_short form or normal form are expressed in the RNA library.

For each tissue, the size and DNA concentration of each band were then compared and normalized.

Tissue distribution of the two isoforms was analyzed by migration on Agilent Bioanalyzer, and the observed relative levels of expression can compared in terms of percentage of expression in the tissues where the expression is the highest:

As shown in FIG. 3 and Table 1, the two BCMA forms do not have the same profile of tissue distribution (FIG. 3: left columns: wild %, right columns: varient %). In particular, the shorter variant form is more expressed in most of the tissues, and particularly in liver, pancreas, brain, and testis. Expression of human BCMA is found in lung, lymph node, mammary gland and blood. Expression of mouse BCMA has been detected in colon, mammary gland and stomach.

C. Biological Activity of the Variants

The biological activity of the polypeptides of this invention can be verified using several biological assays that are known per se in the art. The polypeptide can be injected directly (sc, ip, iv) in the animal or delivered using, e.g., FAST TRACK technologies (EP 04405494.8).

BCMA Variants Compete with BCMA for APRIL

The BCMA variants of the present invention retain the ligand binding domain of BCMA. The ability of BCMA variants to compete with BCMA for the ligand APRIL can be tested by the following assay using a BIACORE 3000 (Uppsala, Sweden).

BCMA protein is produced and purified from CHO cells according to methods well known in the art. Appropriate dilutions of BCMA protein are immobilized on a Sensor Chip such as a CM5 using BIACORE 3000 standard amine coupling procedure. Purified APRIL protein is added to the chip in the presence and absence of purified BCMA variants. Using methods well known in the art and following the standard BIACORE 3000 manufacturers instructions, the ability of BCMA variants to compete for APRIL binding can be detected. In the absence of BCMA variant protein, APRIL will be shown to bind to immobilized BCMA as detected by BIACORE technology. In the presence of BCMA variants, the binding of APRIL to immobilized BCMA will be reduced, indicating that BCMA variants compete with BCMA for binding of APRIL. As a positive control, antibodies which block the binding of APRIL to BCMA may be used.

BCMA Variants Reduce the Number of Circulating B-Cells in Normal Mice

BCMA has been associated with B-cell development and proliferation, through the action of its ligands, Blys and APRIL. The ability of BCMA variants to antagonize the activity of ligands of BCMA, and cause a reduction in the number of circulating B-cells in normal mice can be determined by B-cell proliferation assays as known in the art and as described in US20030082175.

BCMA Variants Cause a Reduction in Tumor Volume in Athymic Mice

Antagonists of BCMA activity have been described as having the ability to reduce the tumor volume in athymic mice injected with a number of tumor cell lines. (US20030082175). BCMA variants can be tested as described in US20030082175. Athymic mice are injected with either purified BCMA variant protein, saline, negative control protein or a positive control protein. The tumor size is measured at an appropriate time after injection, e.g. 30 to 45 days. BCMA variants of the present invention will significantly reduce the tumor volume as compared to untreated or those treated with negative control protein.

TABLE 1

| Tissue | Normal % | Variant % |
|---|---|---|
| small intestine | 100 | 54 |
| normal adipose | 1 | 20 |
| brain | 0 | 26 |
| testis | 17 | 100 |
| liver | 11 | 99 |
| pancreas | 0 | 75 |
| skeletal muscle | 1 | 24 |

REFERENCES

Gross J A, Johnston J, Mudri S, Enselman R, Dillon S R, Madden K, Xu W, Parrish-Novak J, Foster D, Lofton-Day C, Moore M, Littau A, Grossman A, Haugen H, Foley K, Blumberg H, Harrison K, Kindsvogel W, Clegg C H. TACI and BCMA are receptors for a TNF homologue implicated in B-cell autoimmune disease. Nature. 2000 Apr. 27; 404 (6781):995-9.

Hatzoglou A, Roussel J, Bourgeade M F, Rogier E, Madry C, Inoue J, Devergne O, Tsapis A. TNF receptor family member BCMA (B cell maturation) associates with TNF receptor-associated factor (TRAF)1, TRAF2, and TRAF3 and activates NF-kappa B, elk-1, c-Jun N-terminal kinase, and p38 mitogen-activated protein kinase. J. Immunol. 2000 Aug. 1; 165(3):1322-30.

Khare S D, Sarosi I, Xia X Z, McCabe S, Miner K, Solovyev I, Hawkins N, Kelley M, Chang D, Van G, Ross L, Delaney J, Wang L, Lacey D, Boyle W J, Hsu H. Severe B cell hyperplasia and autoimmune disease in TALL-1 transgenic mice. Proc Natl Acad Sci USA. 2000 Mar. 28; 97(7):3370-5.

Kim H M, Yu K S, Lee M E, Shin D R, Kim Y S, Paik S G, Yoo O J, Lee H, Lee J O. Crystal structure of the BAFF-BAFF-R complex and its implications for receptor activation. Nat Struct Biol. 2003, 10(5):342-8.

Laabi Y, Gras M P, Carbonnel F, Brouet J C, Berger R, Larsen C J, Tsapis A. A new gene, BCM, on chromosome 16 is fused to the interleukin 2 gene by a t(4;16)(q26;p13) translocation in a malignant T cell lymphoma. EMBO J. 1992 November; 11(11):3897-904.

Laabi Y, Gras M P, Brouet J C, Berger R, Larsen C J, Tsapis A. The BCMA gene, preferentially expressed during B lymphoid maturation, is bidirectionally transcribed. Nucleic Acids Res. 1994; 22(7):1147-54.

Liu Y, Hong X, Kappler J, Jiang L, Pan C H, Martin W E, Murphy R C, Shu H B, Zhang G. Ligand-receptor binding revealed by the TNF family member TALL-1. Nature. 2003 May 1; 423(6935):49-56.

Mackay F, Woodcock S A, Lawton P, Ambrose C, Baetscher M, Schneider P, Tschopp J, Browning J L. Mice transgenic for BAFF develop lymphocytic disorders along with autoimmune manifestations. J Exp Med. 1999 Dec. 6; 190 (11):1697-710.

Mackay F. Et al, BAFF AND APRIL: a tutorial on B cell survival. Annu Rev Immunol, 21:231-264, 2004.

Madry C, Laabi Y, Callebaut I, Roussel J, Hatzoglou A, Le Coniat M, Mornon J P, Berger R, Tsapis A. The characterization of murine BCMA gene defines it as a new member of the tumor necrosis factor receptor superfamily. Int Immunol. 1998 November; 10(11):1693-702.

Marsters S A, Yan M, Pitti R M, Haas P E, Dixit V M, Ashkenazi A. Interaction of the TNF homologues BLyS and APRIL with the TNF receptor homologues BCMA and TACI. Curr Biol. 2000 Jun. 29; 10(13):785-8.

O'Connor B P, Raman V S, Erickson L D, Cook W J, Weaver L K, Ahonen C, Lin L L, Mantchev G T, Bram R J, Noelle R J. BCMA is essential for the survival of long-lived bone marrow plasma cells. J Exp Med. 2004 Jan. 5; 199(1):91-8.

D. R. Patel, H. J. Wallweber, J. Yin, S. K. Shriver, S. A. Marsters, N.C. Gordon, M. A. Starovasnik, and R. F. Kelley. Engineering an APRIL-specific B cell maturation antigen. J Biol Chem, 279 (16):16727-16735, 2004.

P. Rennert, P. Schneider, T. G. Cachero, J. Thompson, L. Trabach, S. Hertig, N. Holler, F. Qian, C. Mullen, K. Strauch, J. L. Browning, C. Ambrose, and J. Tschopp. A soluble form of B cell maturation antigen, a receptor for the tumor necrosis factor family member APRIL, inhibits tumor cell growth. J Exp Med, 192 (11):1677-1684, 2000.

Shu H B, Johnson H. B cell maturation protein is a receptor for the tumor necrosis factor family member TALL-1. Proc Natl Acad Sci USA. 2000 Aug. 1; 97(16):9156-61.

Yu G, Boone T, Delaney J, Hawkins N, Kelley M, Ramakrishnan M, McCabe S, Qiu W R, Kornuc M, Xia X Z, Guo J, Stolina M, Boyle W J, Sarosi I, Hsu H, Senaldi G, Theill L E. APRIL and TALL-I and receptors BCMA and TACI: system for regulating humoral immunity. Nat. Immunol. 2000 September; 1(3):252-6.

Wallweber H J, Compaan D M, Starovasnik M A, Hymowitz S G. The crystal structure of a proliferation-inducing ligand, APRIL. J Mol. Biol. 2004 Oct. 15; 343(2):283-90.

The invention claimed is:

1. An isolated BCMA polypeptide variant comprising SEQ ID NO: 3.

2. The isolated BCMA polypeptide according to claim 1, further comprising an additional amino acid domain that comprises a signal peptide, a tag, a targeting peptide, the constant domain of an immunoglobulin, a multimerization domain or a biologically active protein or fragment thereof.

3. The isolated BCMA polypeptide according to claim 1, wherein said polypeptide further comprises a label, toxin or drug.

4. The isolated BCMA polypeptide according to claim 1, wherein said polypeptide is conjugated to polyethylene glycol.

5. A pharmaceutical composition comprising a polypeptide according to claim 1 and a pharmaceutically acceptable carrier or diluent.

6. An isolated BCMA polypeptide comprising SEQ ID NO: 1 in which amino acid residues 44-93 have been deleted.

7. A pharmaceutical composition comprising a pharmaceutically acceptable carrier or diluent and a polypeptide according to claim 6.

8. An isolated nucleic acid encoding a polypeptide comprising SEQ ID NO: 3.

9. The isolated nucleic acid according to claim 8, wherein said nucleic acid comprises SEQ ID NO: 2.

10. A vector comprising a nucleic acid according to claim 8.

11. An isolated host cell comprising a nucleic acid according to claim 8.

12. The isolated host cell according to claim 11, wherein said host cell comprises a vector, said vector comprising a nucleic acid encoding a polypeptide comprising SEQ ID NO: 3.

13. An isolated nucleic acid encoding a polypeptide comprising SEQ ID NO: 1 in which amino acid residues 44-93 have been deleted.

14. A vector comprising a nucleic acid according to claim 13.

15. An isolated host cell comprising a nucleic acid according to claim 13.

16. An isolated nucleic acid encoding a polypeptide comprising SEQ ID NO: 1 in which amino acid residues 44-93 have been deleted, wherein said polypeptide is fused to an additional amino acid domain that comprises a signal peptide, a tag, a targeting peptide, the constant domain of an immunoglobulin, a multimerization domain or a biologically active protein or fragment thereof.

17. The isolated nucleic acid according to claim 16, wherein said additional amino acid domain comprises the constant domain of an immunoglobulin.

18. A vector comprising a nucleic acid according to claim 16.

19. The vector according to claim 18, wherein said additional amino acid domain comprises the constant domain of an immunoglobulin.

20. An isolated nucleic acid encoding a polypeptide comprising SEQ ID NO: 3 fused to an additional amino acid domain that comprises a signal peptide, a tag, a targeting peptide, the constant domain of an immunoglobulin, a multimerization domain or a biologically active protein or fragment thereof.

21. The isolated nucleic acid according to claim 20, wherein said additional amino acid domain comprises the constant domain of an immunoglobulin.

22. A vector comprising a nucleic acid according to claim 20.

23. The vector according to claim 22, wherein said additional amino acid domain comprises the constant domain of an immunoglobulin.

24. A method of producing a polypeptide comprising culturing a recombinant host cell under conditions allowing expression of a nucleic acid molecule encoding a polypeptide and recovering the polypeptide produced by the expression of said nucleic acid, wherein said nucleic acid encodes:

a) a polypeptide comprising SEQ ID NO: 1 in which amino acid residues 44-93 have been deleted;

b) a polypeptide comprising SEQ ID NO: 3; or c) a polypeptide fragment of a BCMA polypeptide, said fragment comprising a ligand-binding domain comprising amino acid residues 7-41 of SEQ ID NO: 1, 8-41 of SEQ ID NO: 1, or 1-43 of SEQ ID NO: 1, a NF-κB activation domain comprising amino acid residues 119-143 of SEQ ID NO: 1 or 94-184 of SEQ ID NO: 1, amino acid residues 42-46 or 41-47 of SEQ ID NO: 3, and lacking a functional transmembrane domain of a BCMA polypeptide.

25. An isolated polypeptide fragment of a BCMA polypeptide, said fragment comprising a ligand-binding domain comprising amino acid residues 7-41 of SEQ ID NO: 1, 8-41 of SEQ ID NO: 1, or 1-43 of SEQ ID NO: 1, a NF-κB activation domain comprising amino acid residues 119-143 of SEQ ID NO: 1 or 94-184 of SEQ ID NO: 1, amino acid residues 42-46 or 41-47 of SEQ ID NO: 3, and lacking a functional transmembrane domain of a BCMA polypeptide.

26. The isolated polypeptide fragment according to claim 25, wherein said fragment binds to APRIL or BAFF.

27. The isolated polypeptide fragment according to claim 25, said polypeptide fragment further comprising a label, toxin or drug.

28. The isolated polypeptide fragment according to claim 25, wherein said polypeptide fragment is conjugated to polyethylene glycol.

29. A pharmaceutical composition comprising a polypeptide fragment according to claim 25 and a pharmaceutically acceptable carrier or diluent.

30. An isolated nucleic acid encoding a polypeptide fragment of a BCMA polypeptide, said fragment comprising a ligand-binding domain comprising amino acid residues 7-41 of SEQ ID NO: 1, 8-41 of SEQ ID NO: 1, or 1-43 of SEQ ID NO: 1, a NF-κB activation domain comprising amino acid residues 119-143 of SEQ ID NO: 1 or 94-184 of SEQ ID NO: 1, amino acid residues 42-46 or 41-47 of SEQ ID NO: 3, and lacking a functional transmembrane domain of a BCMA polypeptide.

31. A vector comprising a nucleic acid according to claim 30.

32. A host cell comprising a vector according to claim 31.

33. An isolated antibody or antigen binding fragment that selectively binds to a BCMA polypeptide epitope, said epitope comprising amino acid residues 42-46 or 41-47 of SEQ ID NO: 3.

34. The isolated antibody or antigen binding fragment according to claim 33, said antibody or antigen binding fragment binding to a BCMA polypeptide epitope comprising amino acid residues 42-46 of SEQ ID NO: 3.

35. The isolated antibody or antigen binding fragment according to claim 33, said antibody or antigen binding fragment binding to a BCMA polypeptide epitope comprising amino acid residues 41-47 of SEQ ID NO: 3.

36. The isolated antibody or antigen binding fragment according to claim 33, said antibody or antigen binding fragment further comprising a toxin, label or drug.

37. A pharmaceutical composition comprising an isolated antibody or antigen binding fragment according to claim 34 and a pharmaceutically acceptable carrier or diluent.

38. The pharmaceutical composition according to claim 37, wherein said antibody or antigen binding fragment further comprises a toxin, label or drug.

39. A method of treating a subject comprising administering to a subject having a disease selected from cancer, an immune disorder or an inflammatory disease a composition comprising:

a) a polypeptide comprising SEQ ID NO: 1 in which amino acid residues 44-93 have been deleted;

b) a polypeptide comprising SEQ ID NO: 3; or c) a polypeptide fragment of a BCMA polypeptide, said fragment comprising a ligand-binding domain comprising amino acid residues 7-41 of SEQ ID NO: 1, 8-41 of SEQ ID NO: 1, or 1-43 of SEQ ID NO: 1, a NF-κB activation domain comprising amino acid residues 119-143 of SEQ ID NO: 1 or 94-184 of SEQ ID NO: 1, amino acid residues 42-46 or 41-47 of SEQ ID NO: 3, and lacking a functional transmembrane domain of a BCMA polypeptide.

40. The method according to claim 39, wherein said method is treating a cancer in a subject.

41. The method according to claim 39, wherein said method is treating an immune disorder in a subject.

42. The method according to claim 39, wherein said method inhibits B-cell maturation or growth in a subject.

43. The method according to claim 39, wherein said method treats an inflammatory disease in a subject.

44. The method according to claim 39, wherein said polypeptide comprises SEQ ID NO: 1 in which amino acid residues 44-93 have been deleted.

45. The method according to claim 39, wherein said polypeptide comprises SEQ ID NO: 3.

46. The method according to claim 39, wherein said polypeptide fragment comprises a ligand-binding domain comprising amino acid residues 7-41 of SEQ ID NO: 1, 8-41 of SEQ ID NO: 1, or 1-43 of SEQ ID NO: 1, a NF-κB activation domain comprising amino acid residues 119-143 of SEQ ID NO: 1 or 94-184 of SEQ ID NO: 1, amino acid residues 42-46 or 41-47 of SEQ ID NO: 3, and lacking a functional transmembrane domain of a BCMA polypeptide.

* * * * *

UNITED STATES PATENT AND TRADEMARK OFFICE

CERTIFICATE OF CORRECTION

PATENT NO. : 7,947,805 B2
APPLICATION NO. : 11/722533
DATED : May 24, 2011
INVENTOR(S) : Benedicte Belloir et al.

It is certified that error appears in the above-identified patent and that said Letters Patent is hereby corrected as shown below:

Column 4,
Line 12, "residues in" should read --resides in--.

Column 5,
Line 31, "may determined" should read --may be determined--.
Line 32, "known the" should read --known to the--.
Line 64, "activity" should read --activity.--.

Column 8,
Line 38, "below" should read --below.--.

Column 9,
Line 28, "derived form" should read --derived from--.

Column 13,
Lines 11-13, "include fatty oils, for example, sesame oil, or synthetic fatty acid esters, for example, sesame oil, or synthetic fatty acid esters, for example" should read --include fatty oils, for example, sesame oil, or synthetic fatty acid esters, for example--.

Column 14,
Line 49, "derived form" should read --derived from--.

Column 15,
Line 14, "Hybrodimas" should read --Hybridomas--.

Column 17,
Line 38, "BCMA short:" should read --BCMA_short:--.

Signed and Sealed this
Twenty-third Day of August, 2011

David J. Kappos
*Director of the United States Patent and Trademark Office*

SEQUENCE LISTING

<160> NUMBER OF SEQ ID NOS: 11

<210> SEQ ID NO 1
<211> LENGTH: 184
<212> TYPE: PRT
<213> ORGANISM: Artificial sequence
<220> FEATURE:
<223> OTHER INFORMATION: homo sapiens

<400> SEQUENCE: 1

Met Leu Gln Met Ala Gly Gln Cys Ser Gln Asn Glu Tyr Phe Asp Ser
1 5 10 15

Leu Leu His Ala Cys Ile Pro Cys Gln Leu Arg Cys Ser Ser Asn Thr
20 25 30

Pro Pro Leu Thr Cys Gln Arg Tyr Cys Asn Ala Ser Val Thr Asn Ser
35 40 45

Val Lys Gly Thr Asn Ala Ile Leu Trp Thr Cys Leu Gly Leu Ser Leu
50 55 60

Ile Ile Ser Leu Ala Val Phe Val Leu Met Phe Leu Leu Arg Lys Ile
65 70 75 80

Ser Ser Glu Pro Leu Lys Asp Glu Phe Lys Asn Thr Gly Ser Gly Leu
85 90 95

Leu Gly Met Ala Asn Ile Asp Leu Glu Lys Ser Arg Thr Gly Asp Glu
100 105 110

Ile Ile Leu Pro Arg Gly Leu Glu Tyr Thr Val Glu Glu Cys Thr Cys
115 120 125

Glu Asp Cys Ile Lys Ser Lys Pro Lys Val Asp Ser Asp His Cys Phe
130 135 140

Pro Leu Pro Ala Met Glu Glu Gly Ala Thr Ile Leu Val Thr Thr Lys
145 150 155 160

Thr Asn Asp Tyr Cys Lys Ser Leu Pro Ala Ala Leu Ser Ala Thr Glu
165 170 175

Ile Glu Lys Ser Ile Ser Ala Arg
180

<210> SEQ ID NO 2
<211> LENGTH: 405
<212> TYPE: DNA
<213> ORGANISM: Artificial sequence
<220> FEATURE:
<223> OTHER INFORMATION: homo sapiens

<400> SEQUENCE: 2
atgttgcaga tggctgggca gtgctcccaa aatgaatatt ttgacagttt gttgcatgct 60
tgcatacctt gtcaacttcg atgttcttct aatactcctc ctctaacatg tcagcgttat 120
tgtaatgcaa gatcaggtct cctgggcatg gctaacattg acctggaaaa gagcaggact 180
ggtgatgaaa ttattcttcc gagaggcctc gagtacacgg tggaagaatg cacctgtgaa 240
gactgcatca agagcaaacc gaaggtcgac tctgaccatt gctttccact cccagctatg 300
gaggaaggcg caaccattct tgtcaccacg aaaacgaatg actattgcaa gagcctgcca 360
gctgctttga gtgctacgga gatagagaaa tcaatttctg ctagg 405

<210> SEQ ID NO 3
<211> LENGTH: 135
<212> TYPE: PRT
<213> ORGANISM: Artificial sequence
<220> FEATURE:

<223> OTHER INFORMATION: homo sapiens

<400> SEQUENCE: 3

```
Met Leu Gln Met Ala Gly Gln Cys Ser Gln Asn Glu Tyr Phe Asp Ser
1               5                   10                  15

Leu Leu His Ala Cys Ile Pro Cys Gln Leu Arg Cys Ser Ser Asn Thr
            20                  25                  30

Pro Pro Leu Thr Cys Gln Arg Tyr Cys Asn Ala Arg Ser Gly Leu Leu
        35                  40                  45

Gly Met Ala Asn Ile Asp Leu Glu Lys Ser Arg Thr Gly Asp Glu Ile
    50                  55                  60

Ile Leu Pro Arg Gly Leu Glu Tyr Thr Val Glu Glu Cys Thr Cys Glu
65                  70                  75                  80

Asp Cys Ile Lys Ser Lys Pro Lys Val Asp Ser Asp His Cys Phe Pro
                85                  90                  95

Leu Pro Ala Met Glu Glu Gly Ala Thr Ile Leu Val Thr Thr Lys Thr
            100                 105                 110

Asn Asp Tyr Cys Lys Ser Leu Pro Ala Ala Leu Ser Ala Thr Glu Ile
        115                 120                 125

Glu Lys Ser Ile Ser Ala Arg
    130                 135
```

<210> SEQ ID NO 4
<211> LENGTH: 23
<212> TYPE: DNA
<213> ORGANISM: Artificial sequence
<220> FEATURE:
<223> OTHER INFORMATION: primer

<400> SEQUENCE: 4
gatcatgttg cagatggctg ggc 23

<210> SEQ ID NO 5
<211> LENGTH: 24
<212> TYPE: DNA
<213> ORGANISM: Artificial sequence
<220> FEATURE:
<223> OTHER INFORMATION: primer

<400> SEQUENCE: 5
agtggcactg ctcgagtcga aatg 24

<210> SEQ ID NO 6
<211> LENGTH: 26
<212> TYPE: DNA
<213> ORGANISM: Artificial sequence
<220> FEATURE:
<223> OTHER INFORMATION: primer

<400> SEQUENCE: 6
ttcgccacca tgttgcagat ggctgg 26

<210> SEQ ID NO 7
<211> LENGTH: 41
<212> TYPE: DNA
<213> ORGANISM: Artificial sequence
<220> FEATURE:
<223> OTHER INFORMATION: primer

<400> SEQUENCE: 7
tcaatggtga tggtgatggt gcctagcaga aattgatttc t 41

<210> SEQ ID NO 8
<211> LENGTH: 185
<212> TYPE: PRT
<213> ORGANISM: Artificial sequence
<220> FEATURE:
<223> OTHER INFORMATION: mus musculus

<400> SEQUENCE: 8

```
Met Ala Gln Gln Cys Phe His Ser Glu Tyr Phe Asp Ser Leu Leu His
1               5                   10                  15

Ala Cys Lys Pro Cys His Leu Arg Cys Ser Asn Pro Pro Ala Thr Cys
            20                  25                  30

Gln Pro Tyr Cys Asp Pro Ser Val Thr Ser Ser Val Lys Gly Thr Tyr
        35                  40                  45

Thr Val Leu Trp Ile Phe Leu Gly Leu Thr Leu Val Leu Ser Leu Ala
    50                  55                  60

Leu Phe Thr Ile Ser Phe Leu Leu Arg Lys Met Asn Pro Glu Ala Leu
65                  70                  75                  80

Lys Asp Glu Pro Gln Ser Pro Gly Gln Leu Asp Gly Ser Ala Gln Leu
                85                  90                  95

Asp Lys Ala Asp Thr Glu Leu Thr Arg Ile Arg Ala Gly Asp Asp Arg
            100                 105                 110

Ile Phe Pro Arg Ser Leu Glu Tyr Thr Val Glu Glu Cys Thr Cys Glu
        115                 120                 125

Asp Cys Val Lys Ser Lys Pro Lys Gly Asp Ser Asp His Phe Phe Pro
    130                 135                 140

Leu Pro Ala Met Glu Glu Gly Ala Thr Ile Leu Val Thr Thr Lys Thr
145                 150                 155                 160

Gly Asp Tyr Gly Lys Ser Ser Val Pro Thr Ala Leu Gln Ser Val Met
                165                 170                 175

Gly Met Glu Lys Pro Thr His Thr Arg
            180                 185
```

<210> SEQ ID NO 9
<211> LENGTH: 180
<212> TYPE: PRT
<213> ORGANISM: Artificial sequence
<220> FEATURE:
<223> OTHER INFORMATION: mus musculus

<400> SEQUENCE: 9

```
Met Ala Gln Gln Cys Phe His Ser Glu Tyr Phe Asp Ser Leu Leu His
1               5                   10                  15

Ala Cys Lys Pro Cys His Leu Arg Cys Ser Asn Pro Pro Ala Thr Cys
            20                  25                  30

Gln Pro Tyr Cys Asp Pro Ser Val Thr Ser Ser Val Lys Gly Thr Tyr
        35                  40                  45

Thr Val Leu Trp Ile Phe Leu Gly Leu Thr Leu Val Leu Ser Leu Ala
    50                  55                  60

Leu Phe Thr Ile Ser Phe Leu Leu Arg Lys Met Asn Pro Glu Ala Leu
65                  70                  75                  80

Lys Asp Glu Pro Gln Ser Gly Ser Ala Gln Leu Asp Lys Ala Asp Thr
                85                  90                  95

Glu Leu Thr Arg Ile Arg Ala Gly Asp Asp Arg Ile Phe Pro Arg Ser
            100                 105                 110

Leu Glu Tyr Thr Val Glu Glu Cys Thr Cys Glu Asp Cys Val Lys Ser
        115                 120                 125

Lys Pro Lys Gly Asp Ser Asp His Phe Phe Pro Leu Pro Ala Met Glu
```

```
    130                 135                 140

Glu Gly Ala Thr Ile Leu Val Thr Thr Lys Thr Gly Asp Tyr Gly Lys
145                 150                 155                 160

Ser Ser Val Pro Thr Ala Leu Gln Ser Val Met Gly Met Glu Lys Pro
                165                 170                 175

Thr His Thr Arg
            180


<210> SEQ ID NO 10
<211> LENGTH: 35
<212> TYPE: PRT
<213> ORGANISM: Artificial sequence
<220> FEATURE:
<223> OTHER INFORMATION: BCMA_short

<400> SEQUENCE: 10

Gln Cys Ser Gln Asn Glu Tyr Phe Asp Ser Leu Leu His Ala Cys Ile
1               5                   10                  15

Pro Cys Gln Leu Arg Cys Ser Ser Asn Thr Pro Pro Leu Thr Cys Gln
            20                  25                  30

Arg Tyr Cys
        35


<210> SEQ ID NO 11
<211> LENGTH: 25
<212> TYPE: PRT
<213> ORGANISM: Artificial sequence
<220> FEATURE:
<223> OTHER INFORMATION: BCMA_short

<400> SEQUENCE: 11

Leu Glu Tyr Thr Val Glu Glu Cys Thr Cys Glu Asp Cys Ile Lys Ser
1               5                   10                  15

Lys Pro Lys Val Asp Ser Asp His Cys
            20                  25
```